United States Patent [19]
Liddell et al.

[11] Patent Number: 5,891,936
[45] Date of Patent: Apr. 6, 1999

[54] PRODUCTION OF A POLYMER COMPOSITION

[75] Inventors: John MacDonald Liddell; Neil George, both of Stockton on Tees, United Kingdom; Peter Deryck Turner, Co Waterford, Ireland

[73] Assignee: Monsanto Company, St. Louis, Mo.

[21] Appl. No.: 894,346

[22] PCT Filed: Feb. 12, 1996

[86] PCT No.: PCT/GB96/00305

§ 371 Date: Jan. 6, 1998

§ 102(e) Date: Jan. 6, 1998

[87] PCT Pub. No.: WO96/25452

PCT Pub. Date: Aug. 22, 1996

[30] Foreign Application Priority Data

Feb. 16, 1995 [GB] United Kingdom .................. 9502980
Dec. 21, 1995 [GB] United Kingdom .................. 9526281

[51] Int. Cl.⁶ ....................................................... C08J 3/02
[52] U.S. Cl. ............................................. 523/353; 528/361
[58] Field of Search ................................ 523/353; 528/361

[56] References Cited

U.S. PATENT DOCUMENTS 5,451,456  9/1995  Marchessault ........................ 523/124

FOREIGN PATENT DOCUMENTS 0 535 534  4/1993  European Pat. Off. ......... A61K 9/51
WO 94/07940  4/1994  WIPO ............................... C08J 3/12

*Primary Examiner*—Paul R. Michl
*Attorney, Agent, or Firm*—Gary M. Bond; Arnold, White & Durkee

[57] ABSTRACT

A process of making a polyhydroxyalkanoate PHA latex comprises making a liquid-form solution of such PHA in a water soluble liquid and contacting that solution with water under shear. Suitably the solution is prepared at a temperature between the boiling point of water and 10° C. below the melting point of the PHA as measured by DSC for example by melt separating PHA from a microbiological suspension thereof, dissolving it in the water soluble liquid, and then contacting the solution at over 100° C. with water at 50°–95° C. The water-soluble liquid may be for example 1,2-propandiol or a liquid more volatile than water such as ethanol, propanol or tertiary butanol. A surfactant may be present or added after contacting, for example one providing steric stabilisation such as an acrylic graft copolymer emulsifier.

12 Claims, No Drawings

PRODUCTION OF A POLYMER COMPOSITION

THIS INVENTION relates to the production of a polymer composition containing a polyhydroxyalkanoic acid (PHA), particularly in latex form.

International application PCT/GB95/01925 discloses (a) a process of recovering PHA from a suspension of particles of PHA in water by maintaining the suspension at a temperature at which the PHA melts, at least partly forming a layer of molten PHA, and separating the PHA layer; and (b) a process of making a PHA latex by shearing separated liquid PHA with a surfactant and water.

The specification of that application is incorporated herein by reference. Generally the preferred conditions indicated therein are preferred for the present invention so far as relevant.

According to the invention a process of making an aqueous PHA latex comprises contacting a liquid-form solution of such PHA in a water-soluble liquid with water under shear.

The PHA can be derived from ring-opening or other organic synthesis, but preferably it is microbiologically produced. It may be introduced by dissolving solid PHA purified from non-PHA cell material (NPCM) by way of solvent extraction or NPCM solubilisation. More preferably it is introduced as a component of a slurry or suspension produced by microbiological fermentation followed optionally by NPCM solubilisation but possibly without drying. Such a suspension may have been subjected to process (a) of the said International application, so that the melt-separation effects significant purification of PHA from NPCM.

Starting from a microbiologically produced biomass of PHA-containing cells, any one or a mixture of the following microbiological suspensions can be subjected to melt-separation and dissolving the PHA in the water-soluble liquid:

1. whole biomass as produced by fermentation, possibly concentrated or diluted;
2. cell-broken biomass resulting from thermal or mechanical treatment of 1;
3. the product of treating 1 or 2 with a surfactant;
4. the product of treating 1 or 2 with a hydrolase and/or protease enzyme;
5. the product of treating 1, 2, 3 or 4 with an oxidising agent, preferably in presence of a chelator and/or surfactant.

Alternatively any of such suspensions may be partly or wholly dried and then contacted with the water-soluble liquid.

For each of such suspensions there may be a step of concentration or dilution or solubles separation before melt-separation. For each of the suspensions made by surfactant treatment in particular, it may be desirable to remove any excess surfactant before the melt-separation step.

If the process starts from solid PHA, it may comprise for example heating an aqueous slurry of solid PHA to above the liquefying point of the PHA in presence of the liquid, or liquefying PHA (eg in an extruder) and injecting it into water at above that point.

The process may be carried out by the steps of:

a) pumping any one or a mixture of suspensions 1 to 4 and the water-soluble liquid into a zone maintained at a pressure and temperature at which the PHA and water are both in the liquid state;

b) maintaining said pressure and temperature until the PHA is substantially all in liquid form;

c) allowing the PHA to separate as the lower layer;

d) dissolving the lower layer in the water-soluble liquid and subjecting the solution, surfactant (if present) and water to mixing at a pressure and temperature at which the PHA solution and water are both in the liquid state until a fine dispersion of PHA has formed; and e) cooling and depressurising said fine dispersion.

To limit decrease of PHA molecular weight at the relatively high temperatures involved, the process is preferably carried out continuously.

Suitable PHAs comprise repeating units of formula —O—$C_mH_n$—CO— where m is in the range 1–13 and n is 2m or (except when m is unity) 2m-2. Typically $C_mH_n$ contains 2–5 carbon atoms in the polymer chain and the remainder (if any) in a side chain. In very suitable PHAs m is 3 or 4, n is 2m and especially there are units with m=3 and m=4 copolymerized together with respectively a $C_1$ and $C_2$ side chain on the carbon next to oxygen in the chain. Particular PHAs contain a preponderance of m=3 units, especially with at least 70 mol% of such units, the balance being units in which m=4. The molecular weight of the PHA is for example over 50000, especially over 100000, up to eg $2 \times 10^6$.

PHA of formula I containing only m=3 units is referred to as PHB; PHA containing m=3 and m=4 units is the co-polymer polyhydroxybutyrate-co-valerate PHBV. PHBV preferably contains 4–20% of m=4 units. The PHA can also be a blend of two or more PHAs differing in the value of m. Correspondingly a mixture of starting suspensions is used. A particular example contains:

a) PHA consisting essentially of Formula I units in which 2–5 mol% of units have m=4, the rest m=3; and b) PHA consisting essentially of Formula I units in which 5–30 mol% of units have m=4, the rest m=3. The proportions in such a blend are preferably such as give an average m=4 content in the range 4–20%.

For the PHA-producing microbiological process the microorganism may be wild or mutated or may have had the necessary genetic material introduced into it. Alternatively the necessary genetic material may be harboured by a eucaryote, to effect the microbiological process. Microbiologically produced PHA is chiral (R) and stereospecific.

Examples of suitable microbiological processes are the following:

for Formula I material with m=3 or m=partly 3, partly 4:
 EP-A-69497 (*Alcaligenes eutrophus*);

for Formula I materials with m=3;
 U.S. Pat. No. 4,101,533 (*A. eutrophus*), EP-A-144017 (*A. latus*);

for Formula I material with m=7–13:
 EP-A-0392687 (various Pseudomonas).

The microbiological production of the PHA is preferably carried out in two stages:

a) aerobic growth of microorganisms and b) aerobic fermentation of the resulting organisms in a medium containing a carbon source but deficient in at least one nutrient essential for growth. The deficient nutrient is preferably phosphate.

The surfactant can be cationic, anionic, non-ionic, zwitterionic or contain hydrophilic groups of more than one type. The hydrophobic part of the surfactant preferably contains at least 8, especially 12–20, carbon atoms per hydrophilic group. It may be (almost) wholly aromatic as in sulphonated naphthalenes and naphthyl methanes; or partly aromatic as in alkyl benzene sulphonates or ethoxylates; or wholly aliphatic. Very suitably the surfactant contains a linear alkyl group. If the surfactant is cationic, preferably its hydrophilic part is quaternary ammonium, based for example on tri $C_1$–$C_4$ alkylammonium. If it is anionic, the hydrophilic group is typically sulphate, sulphonate, carboxylate, phosphate or phosphonate. If it is non-ionic, it may be for example an ethoxylate, for example, an alkyl ethoxylate containing 7 to 16 alkyl carbon atoms and up to 100 ethoxylate units, or a block copolymer of ethylene oxide and propylene oxide or an alkylphenyl-ethoxylate. Suitable cationic surfactants include, typically as chloride or bromide: dodecyl-, tetradecyl- and cetyl-trimethyl-ammonium, cetyldimethyl-ethylammonium, dodecyl-, tetradecyl- and hexadecyl-benzyldimethylammonium, benzalkonium, benzethonium, methylbenzethonium and cetylpyridinium. Suitable anionics include, typically as sodium salts: dodecyl sulphate, N-lauroylsarcosinate, dioctylsulfo-succinate, cholate, deoxycholate, laurate, myristate, palmitate, and stearate. Suitable non-ionics include sorbitan monopalmitate, alkylglucosides and nonyl phenylethoxylates. The surfactants preferred are cetyltrimethylammonium bromide and sodium deoxycholate, dodecyl sulphate, N-lauroylsarcosinate and dioctylsulfo-succinate.

The concentration of PHA in the latex is typically 100 to 600, especially 200 to 500, g/l. The concentration of surfactant in or added after the contacting step is typically in the range 0.25 to 10, especially 1 to 5 % w/w on the PHA component of the mixture.

Typical pressures and temperatures for various PHAs are, unless a liquid more volatile than water is used:

|  | Pressure, Pa (bar) | Temperature °C. |
| --- | --- | --- |
| PHA homopolymer | $10^6$ (10) | 180 |
| 97:3 B:V molar | $8 \times 10^5$ (8) | 170 |
| 88:12 B:V molar | $5.4 \times 10^5$ (5.4) | 155 |
| 79:21 B:V molar | $3.7 \times 10^5$ (3.7) | 142 |

The contacting may employ any one or more of the following dispersive means for example:
  fine nozzle(s) or spinnerets, possibly with vibration, possibly ultrasonic; ultrasonic agitation of a sub-zone or larger body of liquid;
  narrow-gap homogenisation such as SILVERSON or ULTRA-TURRAX;
  high pressure homogenisation such as APV Manton-Gaulin, Ronnie or Braun & Luebhe; impingement jet homogenisation; plastic milling such as HOBART, BAKER-PERKINS or WERNER-PFLEIDERER; ball-milling or gravel-milling;
  paddle agitation, toothed impellor agitation. Which of these is used depends on temperatures, pressures and PHA solution viscosity and generally on design convenience.

Conditions in the contacting zone are controlled according to the particle size and particle size distribution of the latex to be produced. Typically the weight average particle size d 50 is in the range 0.05 to 5, especially 0.1 to 1.5, $\mu$m. Average weight average particle sizes d 50 of 0.1–0.4, 0.4–0.6 and 0.8–1.1 $\mu$m appear to be especially suitable for particular applications. The PHA in the particles is preferably at least 96, especially at least 98, % w/w pure. It is preferably low in crystallinity, especially less than 30, particularly less than 20, for example less than 1 percent crystalline as measured by density or wide angle X-ray scattering (WAXS). The percentages are by weight and are believed to represent:

$$\frac{\text{Weight of crystalline PHA}}{\text{total weight of PHA in sample}} \times 100$$

where each particle is either wholly amorphous or crystalline to the full extent practicable.

Use of the water-soluble liquid that dissolves PHA at over 100° C. enables the PHA to flow at a temperature below its melting point, and thus make it possible to use less strongly shearing conditions, since the PHA is precipitated from solution. The extent of water solubility of the liquid should be such that in the contacting step the partition of the liquid is substantially in favour of water. In the simplest case the liquid is water-miscible at ambient temperature. A solubility of at least 1.5, preferably at least 10, g/100 ml water appears to suffice, provided the liquid has a positive temperature coefficient of solubility in water. Partition in favour of water can be assisted by suitable design of the contacting apparatus, for example by turbulence in mixing. Two or more contacting stages can be used in series. If liquid remains in the PHA at the end of high temperature contacting step(s), it will usually be expelled on cooling, as the PHA deposits from solution. Among the liquid usable are ethylene carbonate, propylene carbonate, diols such as ethanediol and 1.2-propanediol, $C_{1-10}$ especially $C_{4-10}$ alkanols, $C_{1-10}$ especially $C_{4-10}$ alkanol acetates, acetone, methyl ethyl ketone, diethyl ketone, methyl isobutyl ketone and cycloalkanones and ethers such as diethyl, diisopropyl and tetramethylene. Co-solvents such as partly esterified or partly etherified glycols can be introduced at this stage.

After the contacting step the latex can undergo one or more of the following treatments:
  concentration or dilution;
  removal of NPCM solubles;
  removal of excess surfactant, addition of further or different surfactant
  addition of thickener or stabiliser
  addition of pigment or co-solvent.

If the latex is subjected to concentration and/or removal of NPCM solubles, this is effected preferably in conditions not provocative of agglomeration or crystallisation. Thus if centrifugation is used, it is preferably at a low g-value or continuous. Washing is preferably by micro-filtration or dia-filtration, since these readily avoid bringing the latex to a concentration high enough to lead to shear-thickening. A typical content of PHA after the contacting step is 0.5 to 1.5% w/w. This is conveniently raised to 1.5 to 5% by micro-filtration.

These precautions apply especially when a low or zero surfactant concentration is present. When, however, the surfactant concentration is higher, for example in the range 1 to 7% w/w on PHA dry solid, the latex can be concentrated to 25–50% solids, for example by evaporation at subatmospheric pressure.

Among preferred operating conditions are:
  1 the solution of PHA is prepared at a temperature between the boiling point of water and 10° C. below the melting point of the PHA as measured by DSC;
  2 the solution of PHA at over 100° C. is contacted with water at a temperature in the range 50°–95° C. at one atmosphere pressure. As a result, the water-soluble liquid can be or include one having substantial (e.g. at least 20% w/w) solubility at 50° C. and up to the temperature of the PHA solution, even though its solubility at ambient temperature is low;

3 from among the liquids specified above, a liquid more volatile than water is selected. Particular such liquids are ethanol, propanols and tertiary butanol. Whichever of the liquid types is used, it is believed that mechanism of formation of the PHA particles is predominantly precipitation from solution;

4 whichever starting material is used, whether a suspension as listed above or PHA previously recovered as solid, the solution preferably is filtered before contacting it with water. Such filtration removes from the PHA solid impurities such as residual NPCM, and generally such as may interfere with film formation by the product latex. Thus if the process starts from solid PHA, that PHA need be less pure (e.g. 85–95%) then when it is to be melt-processed (over 95%);

5 if a surfactant is present at the contacting stage or is added thereafter, there may be used, instead of or in addition to the surfactants disclosed above, an agent providing steric stabilisation, especially a water-soluble copolymeric dispersant.

Co-polymeric dispersants are characterised by containing a plurality—at least 2 and typically at least 10 and up to e.g. several hundred—of repeating units, including units of two types:

A PHA—compatible; and
B hydrophilic.

Type A units may be for example aliphatic hydrocarbon (for example as in addition polymers) or aromatic hydrocarbon or (in chain lengths sufficient to give water-insolubility in a corresponding polymer consisting of such units) polyoxyalkylene, especially poly-1,2-propylene oxide or polyester of the head-to-tail or head-to-head/tail-to-tail types such as for example, 12-hydroxy stearic acid polycondensate or alkyd resin.

Preferably type A units carry substituents such as esterified carboxy groups or esterified or etherified hydroxy groups or both, since these afford greater compatibility with the PHA and are characteristic of compounds effective as plasticisers for PHA. Particular examples of such substituents are disclosed below.

Type B units can be anionic, for example carboxylate, sulphate, sulphonate, phosphate or phosphonate; or cationic, for example ammonium, especially quaternary ammonium; or non-ionic, for example polyalkylene oxide especially polyethyleneoxide, or polyglycerol or sorbitan or glycoside or amine oxide. The dispersant may contain hydrophilic groups of more than one chemical composition or ionic category. Very suitably it is polyethyleneoxy, especially 10 to 100 ethylene oxide units long, as is typical of conventional water-soluble surfactants.

The dispersant may contain a minor proportion, for example under 20 mol percent, of units falling into neither type A nor type B.

The balance of type A and type B units should be such as to provide the water solubility, which typically is at least 1% w/w in water at 20° C. Preferably the type B units are in a minority by moles, for example less than one-third of the total units in the copolymer chain; correspondingly the water-soluble portion of the type B units, if polyethyleneoxy, should be sufficiently long. The HLB number (HLB signifies hydrophile-lipophile balance rating) of the dispersant is suitably in the range 10–15. Generally the dispersant is preferably from the class of non-ionic emulsifiers, especially when the PHA particles are non-crystalline to the extent described below.

In a particular dispersant there may be present units carrying at least one oxygen-linked hydrocarbon group. The oxygen-links may be ester or ether. Examples of esters are:

(a) those of the acids acrylic (as hereinafter defined), maleic, fumaric and itaconic, with $C_{1-18}$ alcohols and phenols;

(b) those of allyl alcohol or the notional vinyl alcohol with $C_{1-18}$ carboxylic acids. Examples of ether groups are those of allyl alcohol or the notional vinyl alcohol with $C_{1-18}$ alcohols and phenols. Such alcohols and carboxylic acids can be straight-chain, branched or cyclic but, if substituted, do not include groups conferring water-solubility on the polymer in the proportion used.

The above-mentioned esterifying alcohols and carboxylic acids and etherifying alcohols preferably each contain at least 2, preferably up to 9, carbon atoms.

Other type A units can be the residues of for example one or more of ethylene, propylene, styrene, vinyl halides, vinylidene halides, vinyl methyl ether, vinyl acetals, vinyl carbonate, acrylic (as hereinafter defined) nitrile or methyl ester and conjugated olefins.

The term 'acrylic' is herein defined by the general formula:

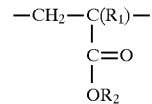

where $R_1$ is hydrogen, $C_{1-12}$ alkyl (especially methyl), cycloalkyl, aryl, halogen or cyano and $R_2$ is a $C_{1-18}$ hydrocarbon group. The analogous definition of $R_1$ applies to corresponding nitrile units if present.

The process is conducted preferably to produce a dispersion in which the PHA particles are on average preferably under 30, especially under 20, especially under 1, % w/w crystalline. It appears that each individual particle is either maximally or 0% crystalline: thus the percentage crystallinity is the weight proportion of maximally crystalline particles. It is believed that the effectiveness of the dispersant may be due to surface mixing or deeper mixing of its type A domain with non-crystalline PHA. Contacting PHA particles with the dispersant is at a temperature preferably over 5° C., for example 10°–50° C.

The molten or dissolved PHA may contain polymer processing additives such as pigments, fillers, plasticisers or other polymers. If these are not soluble in the PHA or its solution they should of course be added after the filtration step.

The latex may be used as such, as for example a coating for paper, polymer films, non-woven boards or foodstuffs. It may alternatively be an intermediate for making dry PHA to be processed as melt or in solution. Such a route may be shorter than conventional routes and, in any event, would permit latex and dry PHA to be made in a single- stream process.

EXAMPLE 1

Solid PHBV (18 mol % V; 50g) was dissolved in propan-1,2-diol (450 g) at 140° C. The solution was filtered at 140° C. through a 40–100 $\mu$m sintered glass filter. It was divided (for apparatus limitations) into 3 approximately equal parts and contacted with water (10 volumes) as follows:

Parts 1 and 2: injected by means of a syringe (1 mm needle internal diameter)

Part 3 poured

In each contacting the water was agitated by a paddle stirrer at 140 rpm. Each resulting mixture was allowed to cool to 40° C. Then to each was added N-lauroylsarcosine sodium salt (75% w/w on the PHBV). The suspensions were stirred gently overnight, sampled (A) and combined, giving a total of 5.5 kg suspension of 0.91% solids content. The suspension was subjected to dia-filtration to 2% w/w solids content on a Sartorius membrane of 0.1 μm pore diameter, washed three times with de-ionised water to remove propan-1,2-diol, and concentrated to 4% w/w solids on the membrane. Further surfactant was added to bring its content to 5% w/w on the PHBV. The suspension was sampled (B), concentrated to 40% w/w solids by rotary evaporation under reduced pressure at 45° C., and sampled (C). The particle sizes of the samples are shown in Table 1.

TABLE 1

| Sample | | Particle Size μm | | |
|---|---|---|---|---|
| | | D10 | D50 | D90 |
| A | injected | 0.22 | 0.36 | 0.57 |
| | injected | 0.20 | 0.39 | 0.99 |
| | poured | 0.24 | 0.58 | 2.10 |
| | combined | 0.21 | 0.42 | 1.33 |
| B | washed, surfactant content made up | 0.19 | 0.39 | 1.19 |
| C | after concentration to 40% w/w | 0.17 | 0.38 | 12.29* |

*This high value is believed to be the result of a temporary loss of agitation in the evaporator, and therefore to be atypical.

EXAMPLE 2

Example 1 (injection) was repeated to the end of the step of cooling to 40° C. Then three samples were taken and treated as follows:

D: control, without addition;

E: addition of N-lauroylsarcosine sodium salt 5% w/w on PHBV;

F: addition of "HYPERMER CG6" (RTM) 5% w/w on PHBV. (HYPERMER CG6 is an acrylic graft copolymer emulsifier formulation in water/propylene glycol containing 32% w/w of active agent of HLB number approximately 11/12, available from Imperial Chemical Industries PLC).

To obtain a measure of stability, the particle size of the samples was measured initially and after 66 hours without and with paddle agitation ( 500 rpm). Results are shown in Table 2

TABLE 2

| Sample | Particle Size μm | | |
|---|---|---|---|
| | D10 | D50 | D90 |
| D - Control - Initial | 0.23 | 0.37 | 0.58 |
| 66 h still | 0.17 | 0.39 | 20.00 |
| 66 h agitated | 8.55 | 30.21 | 65.55 |
| E - Sarcosine - Initial | 0.22 | 0.38 | 0.69 |
| 66 h still | 0.20 | 0.41 | 13.67 |
| 66 h agitated | 3.14 | 38.17 | 64.48 |
| F - CG6 - Initial | 0.22 | 0.38 | 0.68 |
| 66 h still | 0.19 | 0.51 | 15.28 |
| 66 h agitated | 0.18 | 0.62 | 45.45 |

It is evident that the sarcosine surfactant limits to some extent the formation of large particles in non-agitated storage and the loss of small particles in agitated storage; the polymeric dispersant CG6, however, is much more effective in these respects.

EXAMPLE 3

A sample of the 40% w/w solids suspension produced in Example 1 was applied to cellulose fibre board 280 g m$^{-2}$ (Hermiboard BO16 from Cascades Blendecques SA) by means of a large K hand coater (R K Print-Coat Instruments Limited, Royston, UK) using a rod giving a 12 μm wet coat thickness. The coated board was dried in ambient air or in an air circulating oven at 130° C. and for 3 min or by infra-red heating at 150° C. for 15 secs. The heated specimens were subjected to the Cobb test for water penetration as follows:

Apparatus conforming to ASTM D2045-64T was used. In this apparatus a weighed coated board sample is clamped coating side upwards to the end of a metal cylinder and water is poured into the cylinder. At 30 min the water is poured off and the sample is detached, wiped and weighed. The test was carried out at room temperature. The water penetration, in g per m$^2$ was:

Oven dried 30

Infra-red 50

The specimen dried in ambient air was observed to have formed a film coherent to scratching. It was also examined by density gradient centrifugation (NYCODENZ-RTM) and observed to be non-crystalline.

What is claimed is:

1. A process of making a PHA latex which comprises making a liquid-form solution of such PHA in a water soluble liquid and contacting that solution with water under shear.

2. A process according to claim 1 in which comprises making the solution at a temperature between the boiling point of water and 10° C. below the melting point of the PHA as measured by DSC.

3. A process according to claim 1 which comprises melt separating PHA from a microbiological suspension thereof.

4. A process according to claim 1 which comprises contacting the PHA solution at over 100° C. with water at 50°–95° C.

5. A process according to claim 1 which includes the step of filtering the PHA solution before contacting it with water.

6. A process according to claim 1 in which the water-soluble liquid is 1,2-propandiol.

7. A process according to claim 1 in which the liquid is more volatile than water.

8. Process according to claim 7 in which the liquid is selected from the class consisting of ethanol, propanols and tertiary butanol.

9. A process according to claim 1 in which the contacting is effected in absence of surfactant but surfactant is added after contacting.

10. A process according to claim 9 which includes use of surfactant providing steric stabilisation.

11. A process according to claim 10 in which the surfactant is an acrylic graft copolymer emulsifier.

12. A process according to claim 1 in which the PHA comprises repeating units of formula —O—$C_mH_n$—CO— where m is 3 or 4, there are units with m=3 and m=4 copolymerised together with respectively a $C_1$ and $C_2$ side chain on the carbon next to oxygen in the chain and the content of m=3 units is at least 70 mol %.

* * * * *